United States Patent
Sudarsky

(10) Patent No.: US 10,884,490 B2
(45) Date of Patent: Jan. 5, 2021

(54) TRANSFER FUNCTION ADAPTATION IN VIRTUAL REALITY ENVIRONMENTS

(71) Applicant: Siemens Healthcare GmbH, Erlangen (DE)

(72) Inventor: Sandra Sudarsky, Bedminster, NJ (US)

(73) Assignee: Siemens Healthcare GmbH, Erlangen (DE)

(*) Notice: Subject to any disclaimer, the term of this patent is extended or adjusted under 35 U.S.C. 154(b) by 60 days.

(21) Appl. No.: 16/287,132

(22) Filed: Feb. 27, 2019

(65) Prior Publication Data
US 2020/0272229 A1 Aug. 27, 2020

(51) Int. Cl.
*G06F 3/01* (2006.01)
*G06T 15/08* (2011.01)
*G06T 19/20* (2011.01)
*G06F 3/16* (2006.01)

(52) U.S. Cl.
CPC .............. *G06F 3/013* (2013.01); *G06F 3/017* (2013.01); *G06F 3/167* (2013.01); *G06T 15/08* (2013.01); *G06T 19/20* (2013.01); *G06T 2210/41* (2013.01); *G06T 2210/62* (2013.01); *G06T 2219/2012* (2013.01)

(58) Field of Classification Search
CPC .......... G06F 3/013; G06F 3/017; G06F 3/167; G06T 15/08; G06T 19/20; G06T 2210/41; G06T 2210/62; G06T 2219/2012
See application file for complete search history.

(56) References Cited

U.S. PATENT DOCUMENTS

| | | | | |
|---|---|---|---|---|
| 2001/0055016 | A1* | 12/2001 | Krishnan | G06T 19/00 345/424 |
| 2005/0131607 | A1* | 6/2005 | Breed | B60R 21/0152 701/45 |
| 2013/0222384 | A1* | 8/2013 | Futterer | G02B 6/0016 345/426 |
| 2013/0278631 | A1* | 10/2013 | Border | G06F 3/04842 345/633 |
| 2018/0310907 | A1* | 11/2018 | Zhang | G06F 3/0346 |
| 2019/0094981 | A1* | 3/2019 | Bradski | G02B 27/0093 |

(Continued)

OTHER PUBLICATIONS

J. Marks et al. Design galleries: A general approach to setting parameters for computer graphics and animation. In Proc. SIGGRAPH, 1997.

(Continued)

*Primary Examiner* — Ricardo Osorio

(57) ABSTRACT

A method includes presenting an image in a head-mounted display (HMD) controlled by a user. The image is rendered with a transfer function that defines one or more presentation characteristics of voxels in the image. Eye sensors in the HMD are used to determine a region of interest being viewed by the user for longer than a predetermined amount of time. The region of interest comprises a subset of voxels included in the image. The transfer function is automatically adjusted to modify one or more of the presentation characteristics of at least the subset of voxels in response to the region of interest. The presentation of the image in the HMD is modified to present the subset of voxels with modified presentation characteristics.

18 Claims, 4 Drawing Sheets

(56) References Cited

U.S. PATENT DOCUMENTS

2019/0279416 A1* 9/2019 Lee .................. G06T 19/20

OTHER PUBLICATIONS

G. Kindlman et al. "Semi-Automatic Generation of Transfer Functions for Direct Volume Rendering," Proc. 1998 IEEE Symp. Volume Visualization, IEEE CS Press, Los Alamitos, Calif., Oct. 1998, pp. 79-86.
C. Rezk-Salama et al. "Automatic Adjustment of Transfer Functions for 3D Volume Visualization" VMV 2000: 357-364.
M. Fujita et al., "Foveated Real-Time Ray Tracing for Virtual Reality Headset"; Light Transport Entertainment Research; May 2014.
S. Sudarsky U.S. Appl. No. 15/811,796, filed Nov. 14, 2017 and entitled "Transfer Function Determination in Medical Imaging".

* cited by examiner

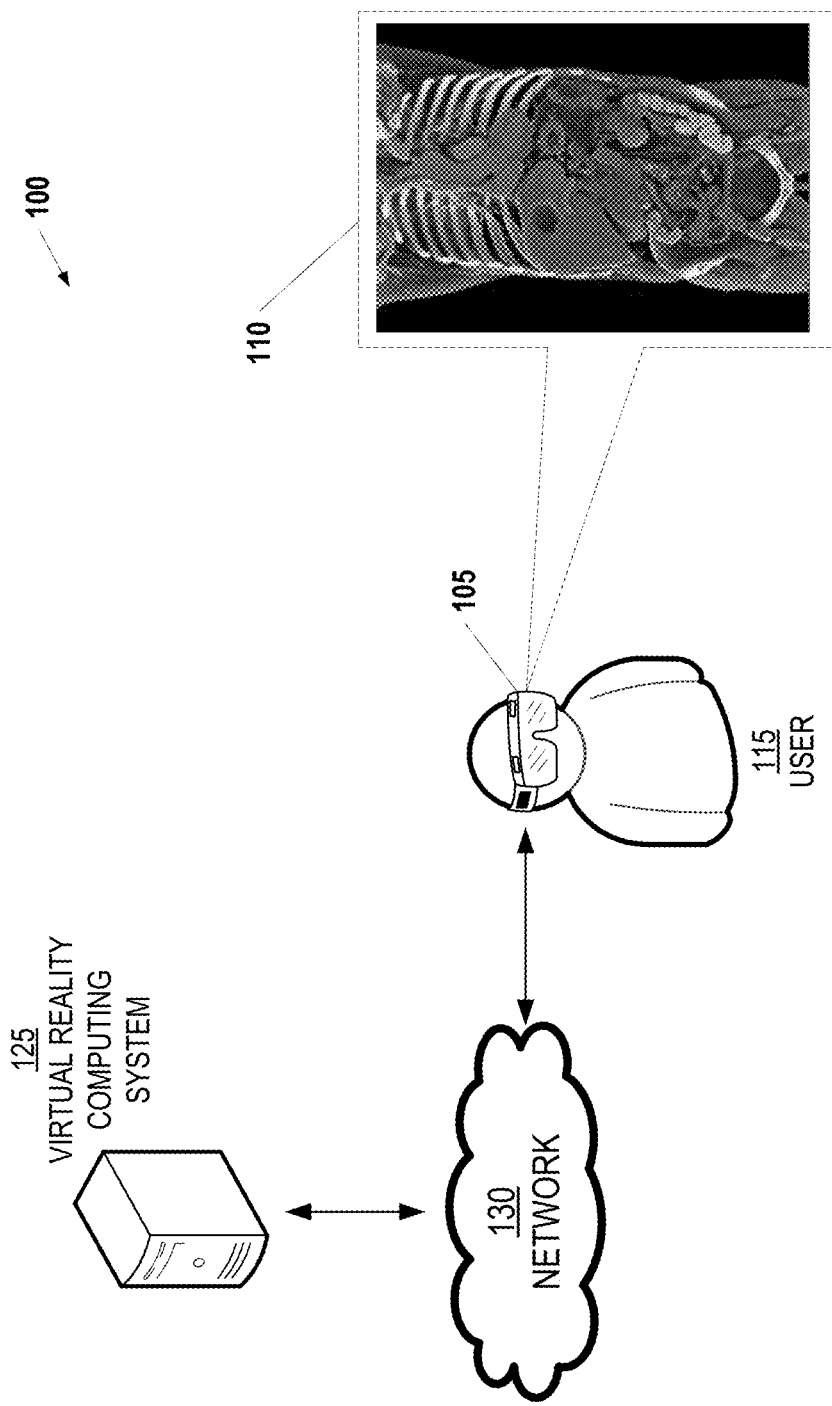

TRANSFER FUNCTION ADAPTATION IN VIRTUAL REALITY ENVIRONMENTS

TECHNICAL FIELD

The present disclosure relates generally to adapting transfer functions for use in a virtual reality (VR) display. The various systems, methods, and apparatuses described herein may be applied to, for example, provide an immersive, interactive visualization of anatomical image data.

BACKGROUND

The immersive experience offered by virtual reality (VR) simulations provides enhanced understanding of complex anatomical structures and offers a free risk, controlled environment in which to practice medical treatments. One of the major obstacles remaining for virtual reality surgery and training is the ability to generate real-time realistic haptic feedback simulation as the user interacts directly with volumetric data.

A central component of volume rendering is a transfer function (TF) that provides a mapping between the values comprising the volume dataset and the optical properties (such as color and opacity) of the rendered image. Most volume rendering systems provide a graphical interface to facilitate the design of these TFs and offer the functionality to manually adjust the parameters that control them. However, the design of TFs remains a difficult problem due to the complex and often unpredictable relationship between TFs and the resulting image. Moreover, in VR environments the interaction with the world should be through natural body movements. Graphical interfaces would compromise the immersive experience offered by VR for training or planning medical procedures. Thus, it is desired to provide methods and systems for adjusting transfer functions within the context of VR applications.

SUMMARY

Embodiments of the present invention address and overcome one or more of the above shortcomings and drawbacks, by providing methods, systems, and apparatuses related to adapting transfer functions (TFs) for use in virtual reality (VR) presentations.

According to some embodiments, a method includes presenting an image in a head-mounted display (HMD) controlled by a user. The image is rendered with a transfer function that defines one or more presentation characteristics of voxels in the image. Eye sensors in the HMD are used to determine a region of interest being viewed by the user for longer than a predetermined amount of time. The region of interest comprises a subset of voxels included in the image. The transfer function is automatically adjusted to modify one or more of the presentation characteristics of at least the subset of voxels in response to the user's viewing of the region of interest. The presentation of the image in the HMD is modified to present the subset of voxels with modified presentation characteristics.

According to other embodiments, a method includes acquiring image scan data with a medical imaging scanner and rendering the image scan data into an image using a first transfer function. This image, comprising a plurality of voxels, is presented in a HMD controlled by a user. Eye sensors in the HMD are used to determine a region of interest being viewed by the user for longer than a predetermined amount of time. The region of interest comprises a subset of voxels included in the image. In response to determining the region of interest, the image scan data is re-rendered into an updated image with a second transfer function that adjusts one or more presentation characteristics for the subset of voxels in comparison to other voxels of the image. Then, the updated image can be presented in the HMD.

In other embodiments, a system comprises a HMD and a computing system. The HMD comprises a monitor and a plurality of eye sensors. The computing system presents an image in the HMD and determines a region of interest being viewed the user for longer than a predetermined amount of time based on data collected by the eye sensors in the HMD. This region of interest comprises a subset of voxels included in the image. Presentation characteristics of the subset of voxels are automatically adjusted in response to determining the region of interest. The presentation of the image in the HMD may then be modified to present the subset of voxels with adjusted presentation characteristics.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 1 shows an example system for presenting interactive visualization in a VR setting, according to some embodiments;

DETAILED DESCRIPTION

Figures 2A, 2B, 2C:
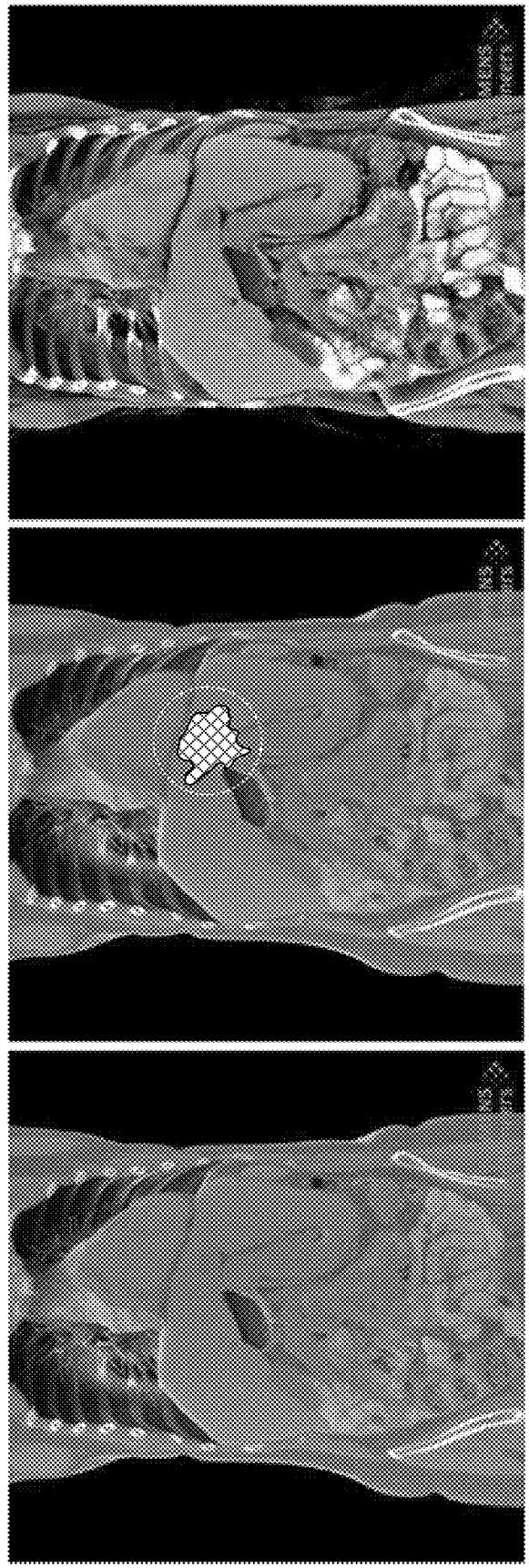
FIG. 2A shows the rendered image using preset values.
FIG. 2B shows an eye tracking result superimposed on the image shown in FIG. 2A.
FIG. 2C shows the resulting image after adjustment of the transfer function based on the ROI defined based on the eye tracking result.

The following disclosure describes the present invention according to several embodiments directed at methods, systems, and apparatuses related to enhancing the presentation characteristics of a region of interest (ROI) within a virtual reality (VR) setting. As described in greater detail in the sections that follow, the techniques described herein monitor a user's gaze in the VR setting while the user views an image. If the user views a particular section of the image for more than a predetermined time (e.g., 3 seconds), a rendering process is triggered that analyzes the characteristics of the voxels within a region of interest defined around the user's gaze and adjusts the transfer function accordingly. This rendering results in enhancement of one or more presentation characteristics within the ROI. The sections that follow describe the invention with respect to contrast adjustment; however it should be understood that the techniques described herein may be used to adjust any other presentation characteristics defined in the transfer function. For example, in other embodiments, presentation characteristics such color, opacity, etc., may be adjusted in addition to, or as an alternative to, contrast. In this way, voxels with different characteristics within the ROI may be easily differentiated in a rendered image.

FIG. 1 shows an example system 100 for presenting interactive visualization in a VR setting, according to some embodiments. A Display Device 105 presents an Image 110 to a User 115. From time to time, for convenience of description, CT imaging data may be used herein as an exemplary imaging modality. It will be appreciated, however, that data from any type of imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention. Furthermore, again for the convenience of description, the techniques describe herein refer to anatomical images; however it should be understood that the disclosed techniques can be readily applied to images that are not anatomical in nature. Additionally, the concepts can be applied to other forms of images including, without limitation holograms.

In the example of FIG. 1, the Display Device 105 is a head-mounted display (HMD) worn by the User 115. In other embodiments, as an alternative, a VR HMD mount may be used that allows the User 115 to insert a smartphone in the mount to be used as the display device. Moreover, it should be understood, that other types of displays generally known in the art can be used with the present invention (e.g., desktop computing monitors, etc.). One example process for displaying three-dimensional images on HMDs is described in U.S. Patent Application Publication No. 20020082498A1, entitled "Intra-operative image-guided neurosurgery with augmented reality visualization" and filed Oct. 5, 2001, the entirety of which is incorporated herein by reference.

A Virtual Reality (VR) Computing System 125 presents images in the Display Device 105 by providing instructions and other data over a Network 130. This Network 130 may generally be any type of network known in the art (e.g., Wi-Fi, Bluetooth, ZigBee, etc.). The VR Computing System 125 provides an immersive experience for the User 115 that connects the visual display presented in the Display Device 105. One example of a VR Computing System 125 is described below with regards to FIG. 4.

The Display Device 105 includes a plurality of eye-tracking sensors (not shown in FIG. 1) that track the gaze of the User 115. In general, any technique known in the art may be used for eye tracking. For example, in one embodiment, the eye tracking sensors each comprise an infrared (IR) light and a camera sensitive to IR. The IR light illuminates the eye of the User 115 and the camera processes the results to determine the location of the pupil of the User 115. Based on this location, the User's 115 gaze can be estimated. In the context of the present invention, the gaze is further used to determine a region of interest (ROI) around the area being viewed by the User 115. For example, in one embodiment, the ROI is a rectangular area centered on the location of the User's 115 gaze. This rectangular area can be sized, for example, based on a user setting or the processing resources available (e.g., from the VR Computing System 125.) In the context of anatomical images, anatomical objects can be segmented from the image using segmentation techniques generally known in the art. Then, the ROI may be constructed such that it frames one or more anatomical objects within the User's 115 gaze. For example, if the User is viewing midsection of a human and the User's 115 gaze is centered on the subject's stomach, the ROI may be defined in a manner that it frames the stomach. If a larger ROI is desired, then other nearby anatomical objects (e.g., the spleen, transverse colon, lobes of the liver, gallbladder, etc.) may also be included to extend the frame of the ROI.

When the User's 115 gaze duration at a particular location is longer than a predetermined amount, the Image 110 displayed to the user is adjusted such that the presentation characteristics of the image are changed to enhance viewing of the ROI. The pre-determined amount that triggers this adjustment may be defined, for example, based on a user setting or a hardcoded value. Ideally the pre-determined amount should be set to a value that ensures that the adjustment process is not performed unnecessarily. For example, the User 115 may specify that a gaze of more than 3 seconds indicates that the adjustment process should be performed.

The adjustment of the ROI may be accomplished in various ways. One example adjustment technique is described in U.S. patent application Ser. No. 15/811,796 filed Nov. 14, 2017 and entitled "Transfer Function Determination in Medical Imaging," (the "'796 application") the entirety of which is incorporated herein by reference. The '796 application describes an image rendering technique that applies transfer functions to histograms of intensity values to modify presentation characteristics such as contrast, opacity, etc. The parameters of the transfer functions may be set based on a ROI. The method described in the '796 application can be adapted in embodiments of the present invention such that, when the gaze duration at a particular location is longer than a predetermined amount, the calculation of a local histogram is triggered and analyzed and the transfer function is automatically adjusted.

The ROI provides an indication of a region that is lacking definition according to some characteristic, such as not having sufficient contrast. For example, for anatomical images, tissue may have a similar intensity as other tissue, so it is rendered in a similar color. To provide more contrast, a transfer function may be set based on the voxels for that tissue designated by the ROI. The transfer function may be set to increase the contrast within the selected region. In another embodiment, the transparency mapped from the transfer function is increased, revealing anatomical structures occluded by the tissue of the ROI. The placement of the ROI based on the user's gaze facilitates exploration of the volumetric data set by interactively defining new transfer functions.

FIGS. 2A-2C show an example of how the ROI-based rendering process can be performed, according to some embodiments. FIG. 2A shows the rendered image using preset values. FIG. 2B shows an eye tracking result (shown in cross hatch with white dotted lines) superimposed on the image shown in FIG. 2A. Finally, FIG. 2C shows the resulting image after adjustment of the presentation characteristics based on the ROI defined based on the eye tracking result. In this case, the ROI is defined such that it covers a possible tumor in the lower abdomen and results in rendering that whole region with increased contrast.

Figure 3:
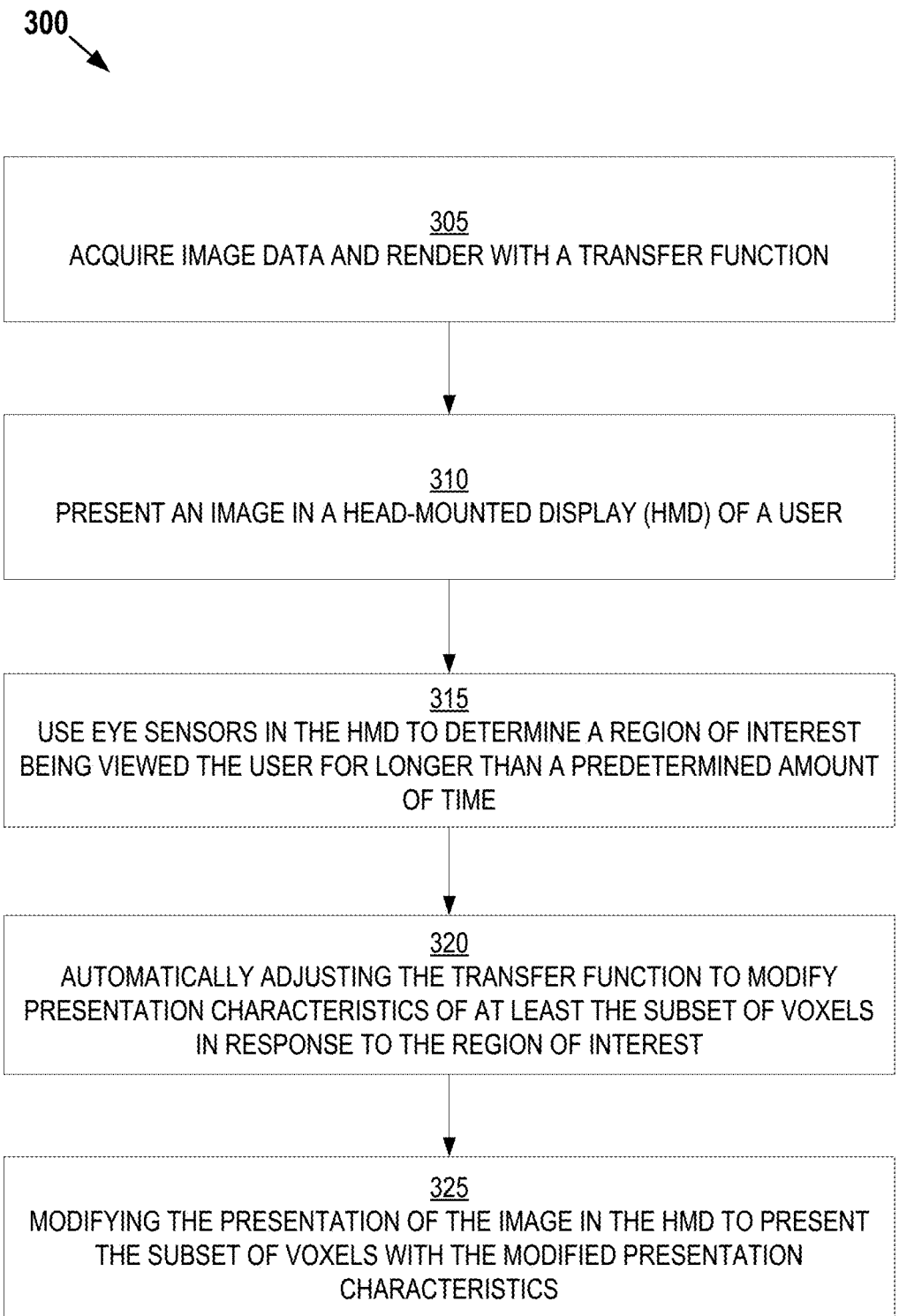
FIG. 3 provides an illustration of using adjusting the transfer function based on a user's gaze, according to some embodiments.

FIG. 3 provides an illustration of adjusting the transfer function based on a user's gaze, for instance, to increase the contrast within the ROI, according to some embodiments. Starting at step 305, an image is acquired that comprises a set of voxels. In general, any image acquisition technique known in the art may be used in acquiring the set of voxels. For example, in medical imaging applications, the set represents a volume of the patient. The volume of a patient is scanned with the medical scanner, such as with magnetic resonance (MR), x-ray (e.g., computed tomography (CT)), ultrasound, or emission tomography (e.g., positron emission tomography (PET) or single photon emission computed tomography (SPECT)). The scan is performed in any format, such as detecting emissions along lines of response, acquiring k-space data at magnetic gradient defined locations, or acquiring projections through the patient with x-rays from different directions.

A renderer of the medical imaging system reconstructs an image volume representing, at least in part, the internal portion of the patient. Any reconstruction from the scan data may be used. Tomography or other process may be used to determine intensities for different locations (i.e., voxels) distributed in three dimensions. As a result of the scan, data representing the interior of the patient in volume is acquired. The reconstruction determines scalar values or intensities for each of a plurality of voxels distributed in three dimensions. These intensities represent response from blood, tissue, bone, other object, and/or contrast agents in the patient.

Any now known or later type of volume rendering may be used. For example, volume ray casting is used. Ray casting projects rays through a volume, such as casting a ray from each pixel of an image plane in parallel or from a view point through the volume. The intensities along each ray are examined to create a pixel value for the image. For example, in maximum intensity projection, the maximum intensity along each ray is found and used. As another example, the intensities along the ray are combined in a weighted average, where the weight is based on opacity or magnitude of the intensity.

In another embodiment, ray tracing is used. Ray tracing is used in physically-based or cinematic rendering to generate photo-realistic images. Rays are projected from each pixel. Light photons are simulated along each of the rays. The scattering, absorption, and/or emission of the light photons may be simulated. The path of the ray may divert due to scattering, providing tracing of the ray through the volume along different paths rather than just the rays from each pixel. Many photons are simulated for each ray. The color or intensity resulting from the scattering, absorption, and/or emission along each ray is calculated. To physically render the image, probabilities are solved.

The probabilities model the interaction of the photons with intensities for the different locations in the volume. For example, Monte Carlo emulation of the photon interaction is used in the rendering. In Monte Carlo-based physical rendering, contribution from the volume samples to the final image are based on simulation of interactions between light photons projected from the viewpoint to the volume structure along the ray paths. The probabilities are solved for along each of a plurality of rays traced from pixels with Monte Carlo ray tracing.

According to various embodiments disclosed herein, the rendering process is performed using a transfer function. The transfer function is a color map used to assign color to scalar values of the scan data. One or more characteristics distinguish one transfer function from another. The characteristics may include, without limitation, the color map or pallet, the opacity (or transparency) level, transparency range or variation, a window width, and/or a window level. The color map controls what colors are assigned to the scalar values. The opacity controls the level of transparency or contribution of any color. The opacity may be one value or may be a range of scalar values over which a given opacity is used. The window width controls the dynamic range or size of the window where colors other than the extremes are used. The window level controls the center of the window along the range of scalar values. Other characteristics include the function for distribution of colors within the window.

Continuing with reference to FIG. 3, at step 310, the image volume generated at step 305 is presented in a head-mounted display (HMD) controlled by a user. Next, at step 315, eye sensors in the HMD are used to determine a region of interest being viewed by the user for longer than a predetermined amount of time. This region of interest comprises a subset of the voxels included in the image. In some embodiments a ROI designator is overlaid over the image to define the spatial extent of the ROI. The ROI may be, for example, a box, oval, circle, or other area designator.

In one embodiment, the subset of voxels in the ROI is identified from a voxel cache or depth map. The depth map provides, for each pixel, a depth at which a given opacity occurs. Various types of depth tests may be used to define the depth. For example, in one embodiment the opacity (e.g., a value) is used. As another example, in other embodiments, a gradient test is performed to find a first gradient above a threshold in the intensities or scalar values traveling from a virtual viewer through the volume. The ROI provides lateral positions corresponding to a group of pixels included in the ROI. The depth map defines a depth for each lateral position. The depth and lateral position define a voxel.

In response to determining the ROI, the transfer function is automatically adjusted to modify one or more of the presentation characteristics of at least the subset of voxels in response to the region of interest. In some embodiments, rather than adjust the original transfer function, a new transfer function is generated based on the intensities of the voxels of the subset. Any characteristic of the intensities may be used, such as a gradient, variance, or curvature (e.g., spatial distribution of structure in the intensities). In some embodiments, the intensity or scalar value from the scan data for the defined voxels are loaded from a voxel cache. Alternatively, in other embodiments, the voxel cache includes the depth map, so the voxel cache is used to determine the intensities for the identified subset of voxels.

In one embodiment, a distribution of the intensities of the voxels of the subset is used at step 320 to adjust the transfer function to modify presentation characteristics of at least the voxels in the ROI. The distribution may be represented by a histogram of scalar values. For example, the number of occurrences of each scalar value or each range of scalar values forms a histogram that may be used as a distribution. Alternatively, a curve may be fit to the histogram and used as the distribution. Any curve or type of curve may be fit. For example, a Gaussian curve is fit to the number of intensities for each scalar value in the histogram. In some embodiments, in order to remove outliers that accidentally fall within the ROI, the characteristics of the fit Gaussian curve are used, ignoring values that lie (e.g., 1, 2, or 3) standard deviations away from the mean. The fit curve has various characteristics, such as a mean and standard deviation. $\mu$ is the mean, and $\sigma$ is the standard deviation of the fitted curve. These characteristics may be used to define distribution.

The distribution is used to create a new transfer function for rendering the voxels. This new transfer function may be similar to the original transfer function used for rendering; however, one or more of the parameters may be adjusted based on the distribution. For example, in one embodiment, the window width and/or window level are changed automatically. The change is to increase contrast for the tissue or structure within the ROI. To increase contrast, the window is centered by a mean for the intensities of the voxels identified by the ROI, and/or the window width is reduced to map the full range of colors to a smaller range of scalar values.

Any function may be used to map the distribution to the window level and/or width. For example, the window width is determined from a mean and standard deviation of the Gaussian curve and a window width of the initial transfer function, and the window level is determined from the window width of the second transfer function, the mean, and the window width of the first transfer function. One possible function to map the window width, W'w, is:

$$W'w = \frac{ROI_{max} - ROI_{min}}{Lut_{max} - Lut_{min}}$$

One possible function to map the window level, W'l, is:

$$W'l = \mu - \frac{Lut_{max} - Lut_{min}}{2} * W'w$$

where $ROI_{min} = \mu - 2\sigma$ and $ROI_{max} = \mu + 2\sigma$, and $Lut_{min}$ and $Lut_{max}$ are the maximum and minimum of the window from the initial transfer function. The difference in $Lut_{max}$ and $Lut_{min}$ is the window width of the initial transfer function.

Other functions or mappings from distribution to window level and/or width may be used. For example, the histogram may not follow a normal or Gaussian distribution, such as where two distributions of any shape are separated by a region of scalar values without occurrence (i.e., fully transparent). The characteristics of the distribution are mapped in a non-linear look-up table to the characteristics of the transfer function.

Additional processing may be performed to further enhance presentation characteristics. For example, to further increase the contrast, the outliers of the intensities (e.g., more than a standard deviation) may be mapped to opaque and transparent. The non-outlier (i.e., remaining) scalar values or intensities may then be distributed over a greater number of colors and/or opacities. Other mappings may be used, such as maintaining higher or lower intensities in the window to provide additional contrast enhancement.

The presentation characteristics can be removed from the image in various ways. For example, in one embodiment, the eye sensors are used to determine that the user's gaze has moved outside of the region of interest. Then, in response to determining that the user's gaze has moved, the image is re-rendered without the presentation characteristic adjustment in the region of interest. In other embodiments, a voice command or a gesture command can be received from user via the HMD requesting that presentation characteristics be removed. In response to receiving this command, the presentation characteristics may then be removed.

Returning to FIG. 3, at step 325 the presentation of the image in the HMD is modified to present the voxels within the ROI with modified presentation characteristics. This modification can be accomplished, for example, by re-rendering the entire image with the new transfer function. Alternatively, only the ROI can be re-rendered and the resulting set of voxels can be overlaid over the existing image or, alternatively, the original voxels in the ROI can be replaced with the presentation characteristic-modified voxels.

Figure 4:
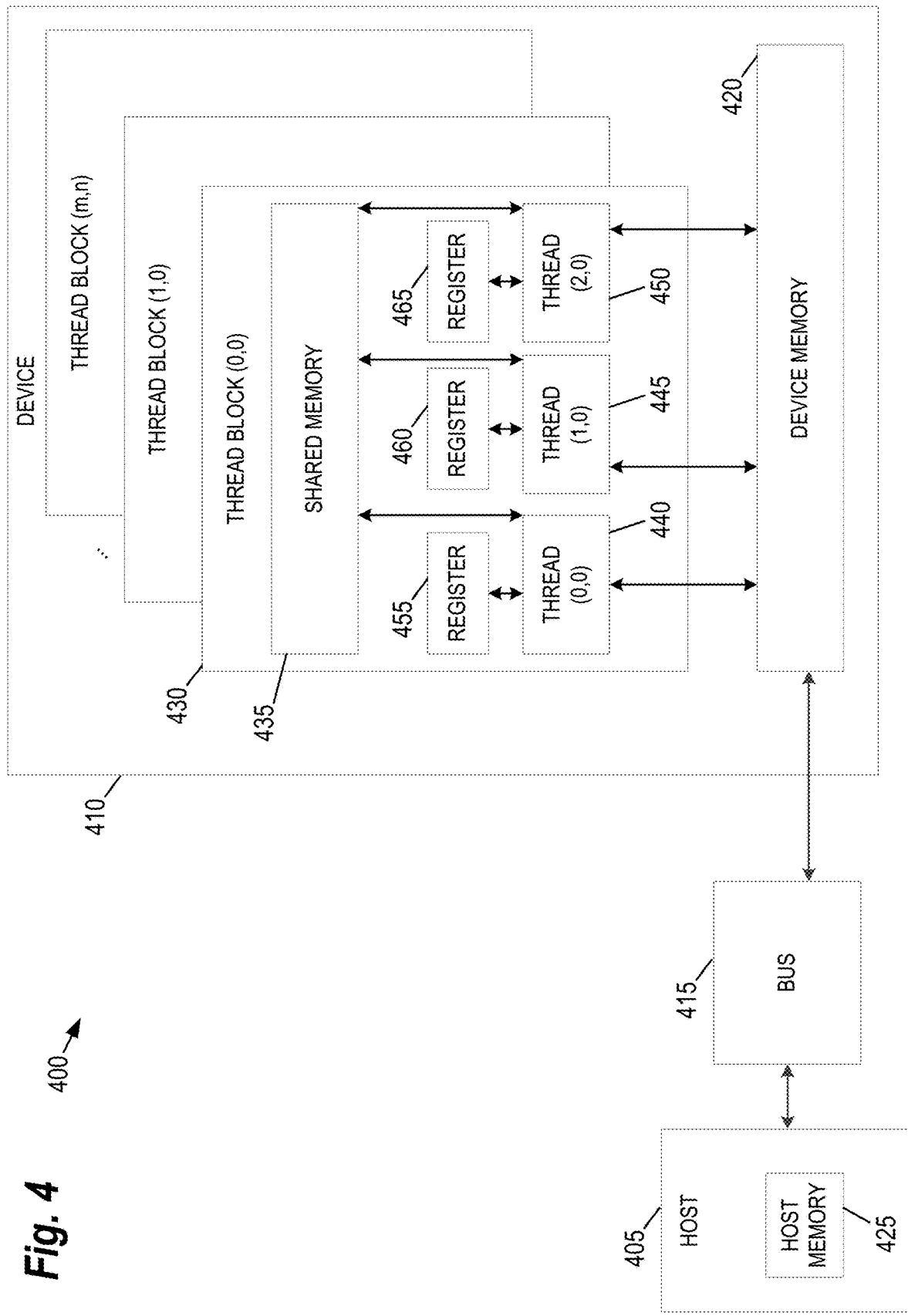
FIG. 4 illustrates an exemplary computing environment within which embodiments of the invention may be implemented

FIG. 4 provides an example of a parallel processing memory architecture 400 that may be utilized to render and present the VR environment discussed above. This architecture 400 may be used in embodiments of the present invention where NVIDIA™ CUDA (or a similar parallel computing platform) is used. The architecture includes a host computing unit ("host") 405 and a GPU device ("device") 410 connected via a bus 415 (e.g., a PCIe bus). The host 405 includes the central processing unit or "CPU" (not shown in FIG. 4) and host memory 425 accessible to the CPU. The device 410 includes the graphics processing unit (GPU) and its associated memory 420, referred to herein as device memory. The device memory 420 may include various types of memory, each optimized for different memory usages. For example, in some embodiments, the device memory includes global memory, constant memory, and texture memory.

Parallel portions of the rendering algorithms may be executed on the architecture 400 as "device kernels" or simply "kernels." A kernel comprises parameterized code configured to perform a particular function. The parallel computing platform is configured to execute these kernels in an optimal manner across the architecture 400 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the architecture 400 of FIG. 4 (or similar architectures) may be used to parallelize rendering tasks. For example, in some embodiments, processing of different subsets of voxels may be performed in parallel.

The device 410 includes one or more thread blocks 430 which represent the computation unit of the device 410. The term thread block refers to a group of threads that can cooperate via shared memory and synchronize their execution to coordinate memory accesses. For example, in FIG. 4, threads 440, 445 and 450 operate in thread block 430 and access shared memory 435. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 4, the thread blocks 430 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. In some embodiments, processing of subsets of the training data or operations performed by the algorithms discussed herein may be partitioned over thread blocks automatically by the parallel computing platform software. However, in other embodiments, the individual thread blocks can be selected and configured to optimize rendering of images. For example, in one embodiment, each thread block is assigned a portion of the overall image.

Continuing with reference to FIG. 4, registers 455, 460, and 465 represent the fast memory available to thread block 430. Each register is only accessible by a single thread. Thus, for example, register 455 may only be accessed by thread 440. Conversely, shared memory is allocated per thread block, so all threads in the block have access to the same shared memory. Thus, shared memory 435 is designed to be accessed, in parallel, by each thread 440, 445, and 450 in thread block 430. Threads can access data in shared memory 435 loaded from device memory 420 by other threads within the same thread block (e.g., thread block 430). The device memory 420 is accessed by all blocks of the grid and may be implemented using, for example, Dynamic Random-Access Memory (DRAM).

Each thread can have one or more levels of memory access. For example, in the architecture 400 of FIG. 4, each thread may have three levels of memory access. First, each thread 440, 445, 450, can read and write to its corresponding registers 455, 460, and 465. Registers provide the fastest memory access to threads because there are no synchronization issues and the register is generally located close to a multiprocessor executing the thread. Second, each thread 440, 445, 450 in thread block 430, may read and write data to the shared memory 435 corresponding to that block 430. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 410 to read and/or write to the device memory. Device memory requires the longest time to access because access must be synchronized across the thread blocks operating on the device. Thus, in some embodiments, the processing of the voxels in the ROI is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 4, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device 105 which displays the image for viewing by the user. The processor, under control of an executable procedure or executable application, manipulates the GUI display images in response to signals received from the input devices. In this way, the user may interact with the display image using the input devices, enabling user interaction with the processor or other device.

As used herein, the term "module" can refer to either or both of: (i) a software component that causes an electronic device to accept various inputs and generate certain outputs; or (ii) an electronic input/output interface, such as a panel, frame, textbox, window or other portion of a GUI.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

We claim:

1. A method comprising:
   presenting an image in a head-mounted display (HMD) controlled by a user, wherein the image is rendered with a transfer function that defines one or more presentation characteristics of voxels in the image;
   using eye sensors in the HMD to determine a region of interest being viewed by the user for longer than a predetermined amount of time, wherein the region of interest comprises a subset of voxels included in the image;
   automatically adjusting the transfer function to modify one or more of the presentation characteristics of at least the subset of voxels in response to the user viewing the region of interest; wherein the one or more presentation characteristics of the subset of voxels are modified by applying the transfer function to a distribution of intensity values corresponding to the subset of voxels;
   modifying the presentation of the image in the HMD to present the subset of voxels with modified presentation characteristics;

wherein modifying the one or more of the presentation characteristics comprises:
determining a first window width used during rendering to map a range of color values to a first set of intensity values for coloring;
re-rendering the subset of voxels using a second window width that maps the range of color values to a second set of intensity values that is smaller than the first set of intensity values, wherein the second window width is smaller than the first window width.

2. The method of claim 1, wherein the presentation characteristics of the subset of voxels are modified by applying the transfer function to a distribution of intensity values corresponding to the subset of voxels.

3. The method of claim 2, wherein the presentation characteristics of the subset of voxels are modified by:
determining a first window level used during rendering to map a range of color values to a first set of intensity values for coloring;
re-rendering the subset of voxels using a second window level that maps the range of color values to a second set of intensity values that is smaller than the first set of intensity values.

4. The method of claim 2, wherein the transfer function modifies the presentation characteristics of the subset of voxels by a process comprising:
identifying outlier intensity values in the distribution of intensity values;
mapping each of the outlier intensity values to an opaque or transparent value.

5. The method of claim 4, wherein the transfer function modifies the presentation characteristics of the subset of voxels further by:
identifying non-outlier intensity values in the distribution of intensity values, wherein non-outlier values are presented in the image using a first predetermined number of colors; and
distributing the remaining intensity values over a second predetermined number of colors that is greater than the first predetermined number of colors.

6. The method of claim 1, wherein the image comprises a plurality of segmented anatomical objects and the region of interest is automatically shaped such that it borders one or more of the segmented anatomical objects being viewed by the user.

7. The method of claim 1, further comprising:
using the eye sensors to determine that the user's gaze has moved outside of the region of interest;
in response to determining that the user's gaze has moved, rendering the image without the modification of the presentation characteristics in the region of interest.

8. The method of claim 1, further comprising:
receiving a voice command from the user via the HMD requesting removal of one or more undesired presentation characteristics in the region of interest; and
in response to receiving the voice command, rendering the image without the undesired presentation characteristics in the region of interest.

9. The method of claim 1, further comprising:
receiving a gesture command from the user via the HMD requesting removal of one or more undesired presentation characteristics in the region of interest; and
in response to receiving the gesture command, rendering the image without the undesired presentation characteristics in the region of interest.

10. A method comprising:
acquiring image scan data with a medical imaging scanner;
rendering the image scan data into an image using a first transfer function, wherein the image comprises a plurality of voxels;
presenting the image in a head-mounted display (HMD) controlled by a user;
using eye sensors in the HMD to determine a region of interest being viewed by the user for longer than a predetermined amount of time, wherein the region of interest comprises a subset of voxels included in the image;
in response to determining the region of interest, re-rendering the image scan data into an updated image with a second transfer function that adjusts one or more presentation characteristics for the subset of voxels in comparison to other voxels of the image; wherein the second transfer function is applied to a distribution of intensity values corresponding to the subset of voxels; and
presenting the updated image in the HMD;
wherein adjusting the one or more presentation characteristics for the subset of voxels comprises:
determining a first window width used during rendering to map a range of color values to a first set of intensity values for coloring; and
re-rendering the subset of voxels using a second window width that maps the range of color values to a second set of intensity values that is smaller than the first set of intensity values, wherein the second window width is smaller than the first window width.

11. The method of claim 10, wherein the second transfer function is applied to a distribution of intensity values corresponding to the subset of voxels.

12. The method of claim 11, wherein the presentation characteristics of the subset of voxels is adjusted by:
determining a first window level used during rendering to map a range of color values to a first set of intensity values for coloring; and
re-rendering the subset of voxels using a second window level that maps the range of color values to a second set of intensity values that is smaller than the first set of intensity values.

13. The method of claim 11, wherein the transfer function adjusts the presentation characteristics of the subset of voxels by a process comprising:
identifying outlier intensity values in the distribution of intensity values; and
mapping each of the outlier intensity values to an opaque or transparent value.

14. The method of claim 13, wherein the transfer function adjusts the presentation characteristics of the subset of voxels further by:
identifying non-outlier intensity values in the distribution of intensity values, wherein non-outlier values are presented in the image using a first predetermined number of colors; and
distributing the remaining intensity values over a second predetermined number of colors that is greater than the first predetermined number of colors.

15. The method of claim 10, further comprising:
using the eye sensors to determine that the user's gaze has moved outside of the region of interest;
in response to determining that the user's gaze has moved, rendering the image without the adjustment of the presentation characteristics in the region of interest.

16. The method of claim 10, further comprising:

receiving a voice command from the user via the HMD requesting removal of the adjustment of the presentation characteristics in the region of interest; and in response to receiving the voice command, rendering the image without the adjustment of the presentation characteristics in the region of interest.

17. The method of claim 10, further comprising:

receiving a gesture command from the user via the HMD requesting removal of the adjustment of the presentation characteristics in the region of interest; and in response to receiving the gesture command, rendering the image without the adjustment of the presentation characteristics in the region of interest.

18. A system comprising:

a head mounted display (HMD) comprising a monitor and a plurality of eye sensors;

a computing system configured to:

present an image in the HMD;

determine a region of interest being viewed by the user for longer than a predetermined amount of time based on data collected by the eye sensors in the HMD, wherein the region of interest comprises a subset of voxels included in the image;

automatically adjust one or more presentation characteristics of the subset of voxels in response to determining the region of interest; and modify the presentation of the image in the HMD to present the subset of voxels with adjusted presentation characteristics, wherein adjusting the one or more presentation characteristics of the subset of voxels comprises:

determining a first window width used during rendering to map a range of color values to a first set of intensity values for coloring; and re-rendering the subset of voxels using a second window width that maps the range of color values to a second set of intensity values that is smaller than the first set of intensity values, wherein the second window width is smaller than the first window width.

\* \* \* \* \*